(12) United States Patent
Podolsky et al.

(10) Patent No.: US 11,660,150 B2
(45) Date of Patent: May 30, 2023

(54) DEXTEROUS 4-DOF SURGICAL TOOL FOR COMPACT ARTICULATION

(71) Applicant: THE HOSPITAL FOR SICK CHILDREN, Toronto (CA)

(72) Inventors: Dale J. Podolsky, Toronto (CA); Thomas Looi, Markham (CA); David Fisher, Toronto (CA); Karen Wong, Toronto (CA); Eric Diller, Toronto (CA); James Drake, Toronto (CA); Christopher Forrest, North York (CA); Gloria Wu, Markham (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 666 days.

(21) Appl. No.: 16/623,524

(22) PCT Filed: Jun. 26, 2018

(86) PCT No.: PCT/CA2018/050789
§ 371 (c)(1),
(2) Date: Dec. 17, 2019

(87) PCT Pub. No.: WO2019/000090
PCT Pub. Date: Jan. 3, 2019

(65) Prior Publication Data
US 2020/0138532 A1     May 7, 2020

Related U.S. Application Data

(60) Provisional application No. 62/524,894, filed on Jun. 26, 2017.

(51) Int. Cl.
*A61B 34/30* (2016.01)
*A61B 17/29* (2006.01)
(Continued)

(52) U.S. Cl.
CPC .............. *A61B 34/30* (2016.02); *A61B 17/29* (2013.01); *A61B 17/3201* (2013.01); *A61B 2034/305* (2016.02); *A61B 2034/715* (2016.02)

(58) Field of Classification Search
CPC ......... A61B 34/30; A61B 34/71; A61B 17/29; A61B 17/3201; A61B 2034/305; A61B 2034/715; A61B 2034/302
See application file for complete search history.

(56) References Cited

U.S. PATENT DOCUMENTS

| 6,902,560 B1 | 6/2005 | Morley et al. |
| 8,540,748 B2 | 9/2013 | Murphy et al. |
| 2013/0144306 A1 | 6/2013 | Stefanchik et al. |

FOREIGN PATENT DOCUMENTS

| CA | 2905048 A1 | 9/2014 |
| CA | 3001935 A1 | 4/2017 |

OTHER PUBLICATIONS

International Search Report dated Oct. 1, 2018, for PCT/CA2018/050789 filed Jun. 26, 20918.

*Primary Examiner* — Brooke Labranche
(74) *Attorney, Agent, or Firm* — Hill & Schumacher

(57) ABSTRACT

A surgical tool for compact articulating during surgical procedures includes a pitch cable, at least one yaw cable, a first link, a second link, at least one end-effector link, and at least one tensioning mechanism. The first link has a pitch joint end with a pitch joint pin and at least one yaw cable guide channel. The second link has a yaw joint end with a yaw joint pin. The second link is rotatably connected to the pitch joint pin. The at least one end-effector link is rotatably connected to said yaw joint pin. The yaw cables are coupled to the end-effector links such that the yaw cables can actuate the end-effector links about the yaw joint pin. The yaw cable guide channel is configured such that the yaw cables travel through a smooth trajectory to the end-effector links. The (Continued)

tensioning mechanism is configured to maintain a constant length.

24 Claims, 21 Drawing Sheets

(51) Int. Cl.
*A61B 17/3201* (2006.01)
*A61B 34/00* (2016.01)

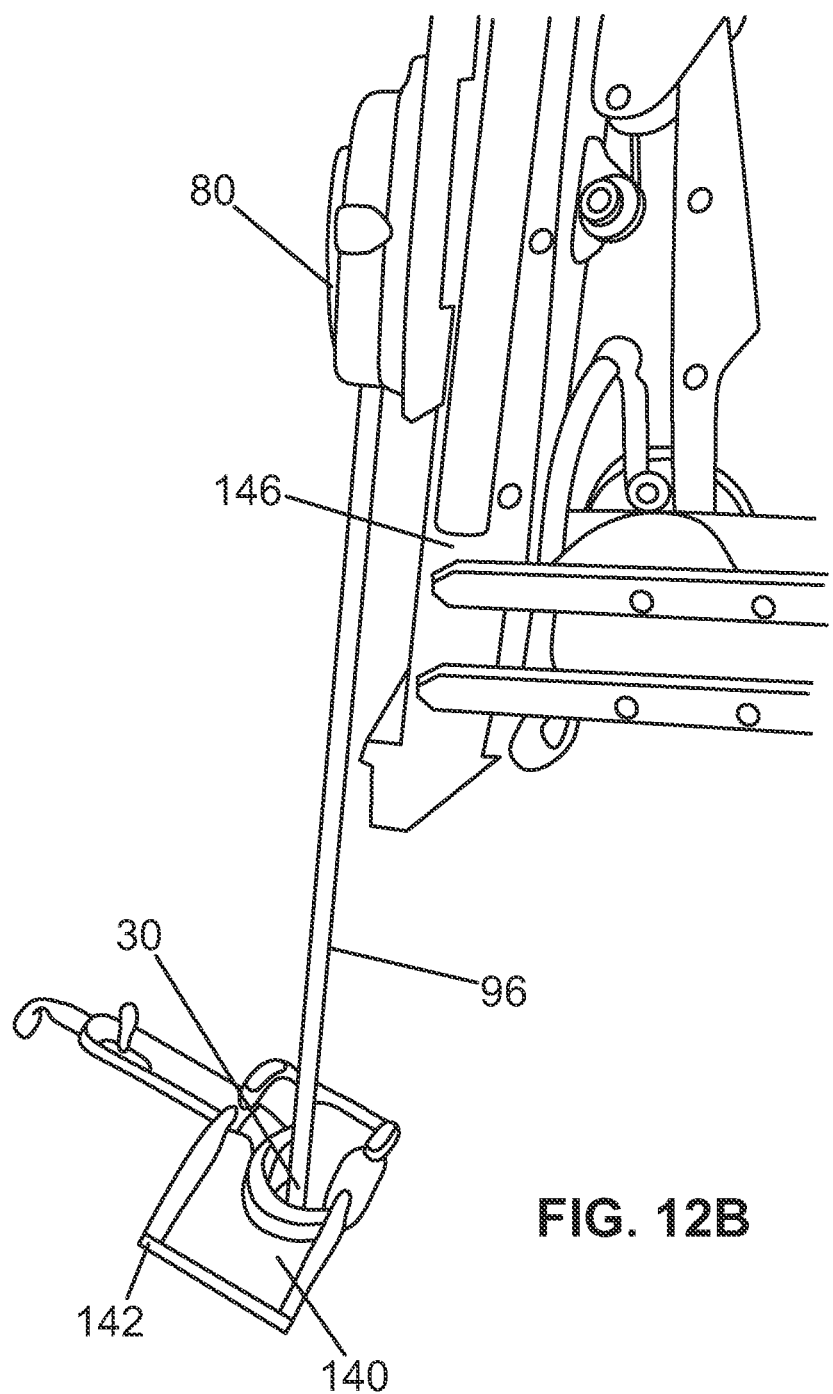

DEXTEROUS 4-DOF SURGICAL TOOL FOR COMPACT ARTICULATION

FIELD

The present disclosure relates to a dexterous 4 degree of freedom (DOF) surgical tool for compact articulation using cable guide channels.

BACKGROUND

Miniaturization of articulation mechanisms is necessary for surgical robotics applications where the goal is to provide high dexterity within increasingly smaller workspaces. A specific example is the oral cavity workspace, where the application of surgical robots with small articulating wristed instruments has achieved success in minimizing the complications of traditional surgery. However, as applications continue to expand to even smaller spaces, such as operating within the small confines of the infant oral cavity, there is a need to develop smaller instruments that can provide high dexterity to perform complex surgical maneuvers.

The development of smaller wrist mechanisms that have 3-degrees-of-freedom (DOF) is difficult at or below 5 mm in diameter. Many different types of wrist designs have been proposed at this size for surgical robotics applications each with specific advantages and disadvantages.

The most successful surgical robot is the da Vinci™ surgical system. The da Vinci™, EndoWrist™ instruments have 3-DOF, can perform complex surgical procedures and rely on a deported actuation system using cables to drive the mechanism. However, they are difficult to maneuver within small body cavities. Miniaturization from 8 mm to 5 mm diameter required redesign from a revolute to multi-backbone mechanism at the expense of performance. If the superior performing revolute joint design can be simplified for further miniaturization, the instrument can provide at least 3-DOF, high dexterity within a more compact mechanism that is more suitable for operating within small body cavities.

Minimizing mechanism length and diameter, while maximizing the size of link components to ensure strength and the allowable cable caliber are competing goals. One method to achieve this is to reduce the number of overall components. An interesting conceptual design is to use solid surface cable guide channels reducing the need for pulleys while maximizing the radius of curvature of the cable paths. Pulleys reduce friction and ensure constant cable circuit lengths during wrist pitch but are difficult to manufacture at small scales and take up valuable space adding length to the mechanism.

The main drawback of solid surface channels are the introduction of increased friction and the potential problems associated therewith such as cable wear, stick slip and hysteresis. One such design has previously been described but never implemented.

SUMMARY

The present disclosure discloses a surgical tool for compact articulating during surgical procedures comprising a pitch cable, at least one yaw cable, a first link having a pitch joint end with a pitch joint pin and at least one yaw cable guide channel; a second link having a yaw joint end with a yaw joint pin, said second link being rotatably connected to the pitch joint pin of the first link, said pitch cable being coupled to said second link such that said pitch cable can actuate said second link about said pitch joint pin; at least one end-effector link being rotatably connected to said yaw joint pin wherein the at least one yaw cables are coupled to said at least one end-effector links such that said at least one yaw cables can actuate said at least one end-effector links about said yaw joint pin; the at least one yaw cable guide channel being configured such that said at least one yaw cables travel through a smooth trajectory to said at least one end-effector links for any angle between said first link and said second link; and at least one tensioning mechanisms configured to maintain a constant length of said at least one yaw cable and to maintain a constant cable tension in said at least one yaw cable for any angle of actuation between said first link and said second link.

In an additional embodiment, the present disclosure discloses a tensioning mechanism having a first pulley, a second pulley, a tensioning pulley being movable relative to said first pulley and said second pulley, and workably connected to a tensioning device, wherein said at least one yaw cable passes around said first pulley to said tensioning pulley, passes around said tensioning pulley to said second pulley and passes around said second pulley; and said tensioning device being able to move said tensioning pulley relative to said first pulley and said second pulley such that the length of said at least one yaw cable between said first pulley and said second pulley changes due to changes in the position of said tensioning pulley. Said at least one tensioning mechanism further has a sliding feature being connected to said tensioning pulley such that said tensioning pulley is movable relative to said first pulley and said second pulley.

In an embodiment, the movement of the sliding featured is induced by a cam slide mechanism having a cam being rotatable about a cam axis such that the position of said cam controls the position of said sliding feature and said tensioning pulley such that the length of said at least one yaw cable between said first pulley and said second pulley increases when said cam pushes said sliding feature away from said cam axis.

A further understanding of the functional and advantageous aspects of the present disclosure can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which:

FIG. 12B is a schematic of a DVRK instrument fitted with the wrist mechanism in a cleft palate setup;

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

In accordance with an embodiment of the invention, a surgical tool is proposed for compact articulation during a surgical procedure which provides three degrees of freedom (pitch, yaw, and end effector motion) for an effector or pair of effectors uses only one pitch cable and several yaw cables. The tool design includes a first link which contains a pin joint defining a pivot axis for pitch control and a second link which defines a second axis for yaw and control of the end effectors. The yaw cables and pitch cables travel along grooved guide channels and can therefore articulate the links and end effectors about the yaw and pivot joints. In particular, the first link can be configured with a variety of cable guide structures which guide opposing sides of the yaw cables. The cable guides are generally curved such that the yaw cables can smoothly travel tangentially across the guide surfaces as the second link pitches. The yaw and pitch cable grooves are further constructed to prevent lateral movement of the cables and the given pitch angle and groove cross section are optimized to reduced friction during the movement of the yaw cables across the guides.

The tool can provide the advantages of enabling compact articulation within confined surgical spaces by reducing the number of tool elements compared to traditional articulating mechanisms, eliminating the space requirements of pulleys thereby allowing a clinically advantageous, reduced working radius for the tool; and accomplishing compact articulation while still being able to provide sufficient tensions to function in high-force surgical applications.

Figure 1A:
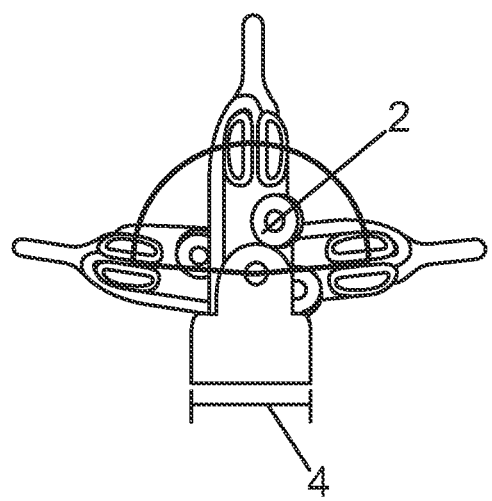
FIG. 1A is a schematic showing the range of motion of a 8 mm end effector on a prior art, standard da Vinci™ robot.
Figure 1B:
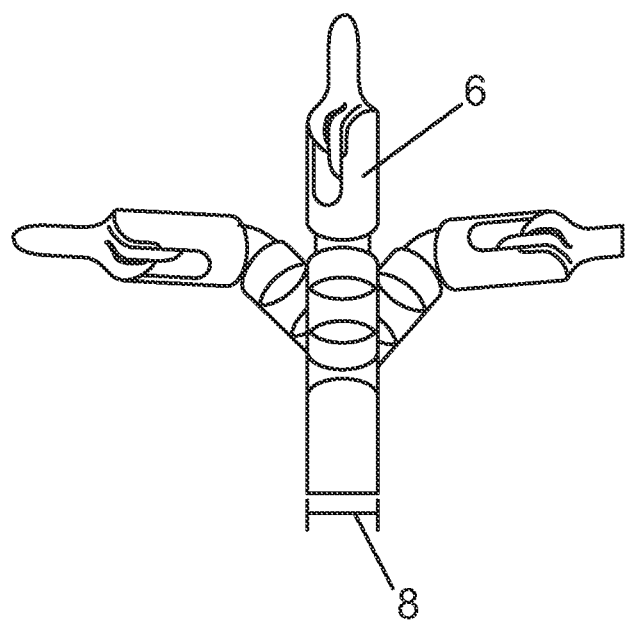
FIG. 1B is a schematic showing the range of motion of a 5 mm end effector on a prior art, standard da Vinci™ robot.
Figure 1C:
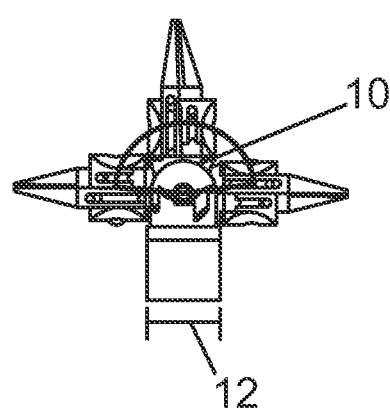
FIG. 1C is a schematic showing the range of motion of the end effector on the proposed wrist mechanism.
Figure 1D:
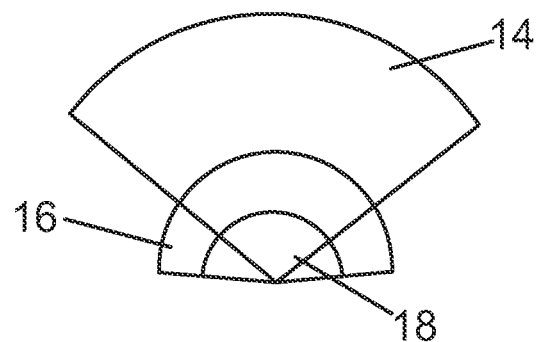
FIG. 1D is a schematic comparison of the pitch-to-yaw axis workspace of three surgical wrist mechanisms.

Referring to FIG. 1A-1D, a diagram of the operating radii for the proposed surgical tool and two configurations (FIG. 1A and FIG. 1B) of the existing "da Vinci™ EndoWrist™" surgical instrument are provided. FIG. 1A displays a configuration of the da Vinci™, EndoWrist™ tool having a shaft diameter 4 of 8 mm and display three position of the tool to illustrate the range of motion of the end effector 2. Likewise, FIG. 1B demonstrates the full range of motion for the end effector 6 of a da Vinci™ EndoWrist™ tool with a shaft diameter 8 of 5 mm. FIG. 1C is an embodiment of the proposed tool with a shaft diameter 12 of 5 mm and a compact articulation of the end effector 10. Lastly, FIG. 1D presents an overlay of the "swept space" required for a full range of motion of the three surgical end effectors. It is apparent that the required swept space for the end effector of the proposed device 18 is significantly less than the swept space required by the 8 mm da Vinci™ configuration 16 or the 5 mm da Vinci™ configuration 14.

Figure 2:
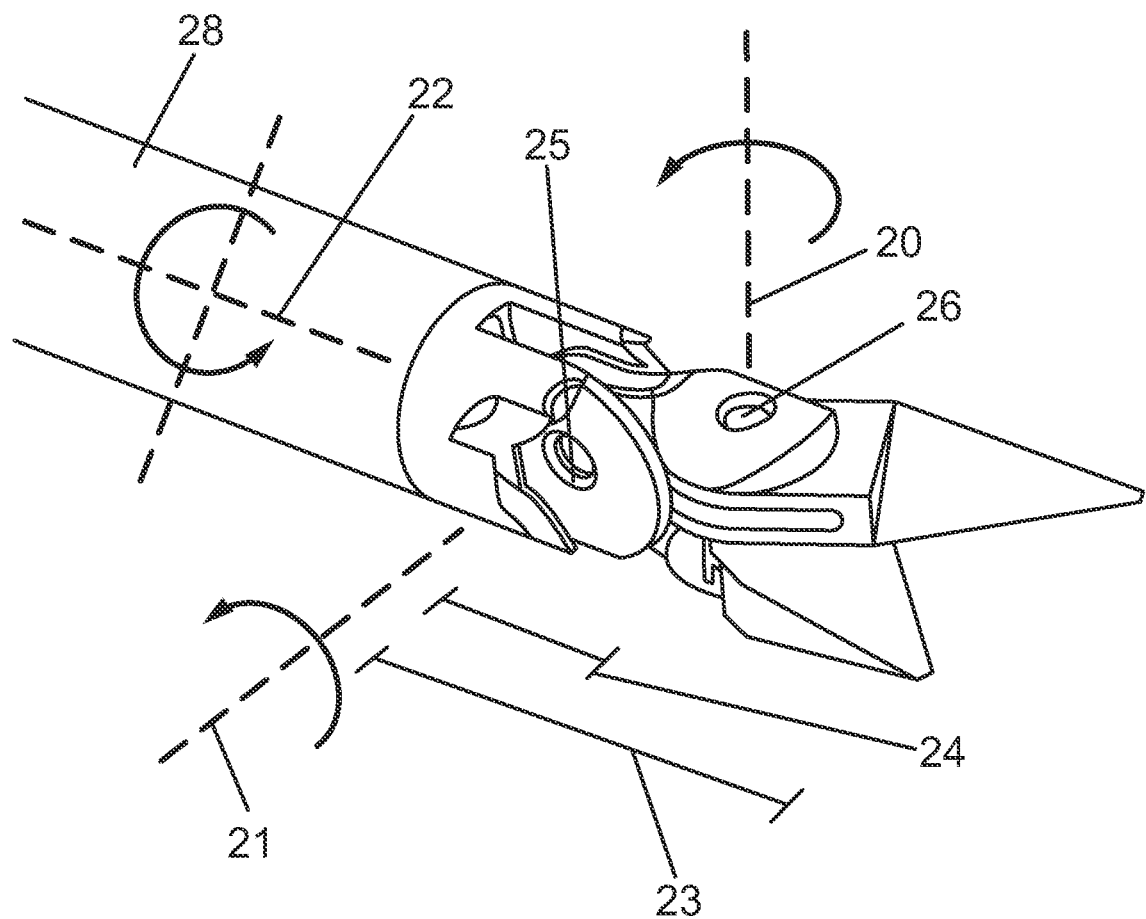
FIG. 2 is a diagram of the wrist mechanism illustrating roll, pitch and yaw motion.

Referring to FIG. 2, an embodiment of the proposed surgical tool is shown illustrating the first and second links and two end effectors connected to the second link. The first link is attached to a mounting shaft 28 which is configured to provide roll motion about the roll axis 22. The first link also comprises a pitch joint pin 25 which enables pitch motion of the second link about a pitch axis 21. Lastly yaw and grip motion of the end effectors about the yaw axis 20 is generally provided by rotation about a yaw joint pin 26 on the second link. Torque for driving the pitch and yaw motion is generally provided by yaw cables, attached to the end effectors and extended down through the guide channels of the first link and, a pitch guide cable extended around the first link and is workably connected to the second link to actuate the linked about the pitch axis 21. In this embodiment, the distance from the pitch axis to the yaw axis 23 (5 mm) and the distance from the pitch axis to the top of the end effectors 24 are also shown. The end effectors include two links, each having a connection portion attached to a circular hub of the second link. The instrument of the end effector is not limited to the "scissor-like" configuration as shown in the embodiment of FIG. 2. A variety of articulating instruments could be introduced as the end effectors of the proposed tool for achieving a variety of functions including but not limited to forceps, surgical grippers, needle drivers, and scissors. The roll motion is actuated by an actuator positioned to rotate the mounting shaft 28.

Figure 3A:
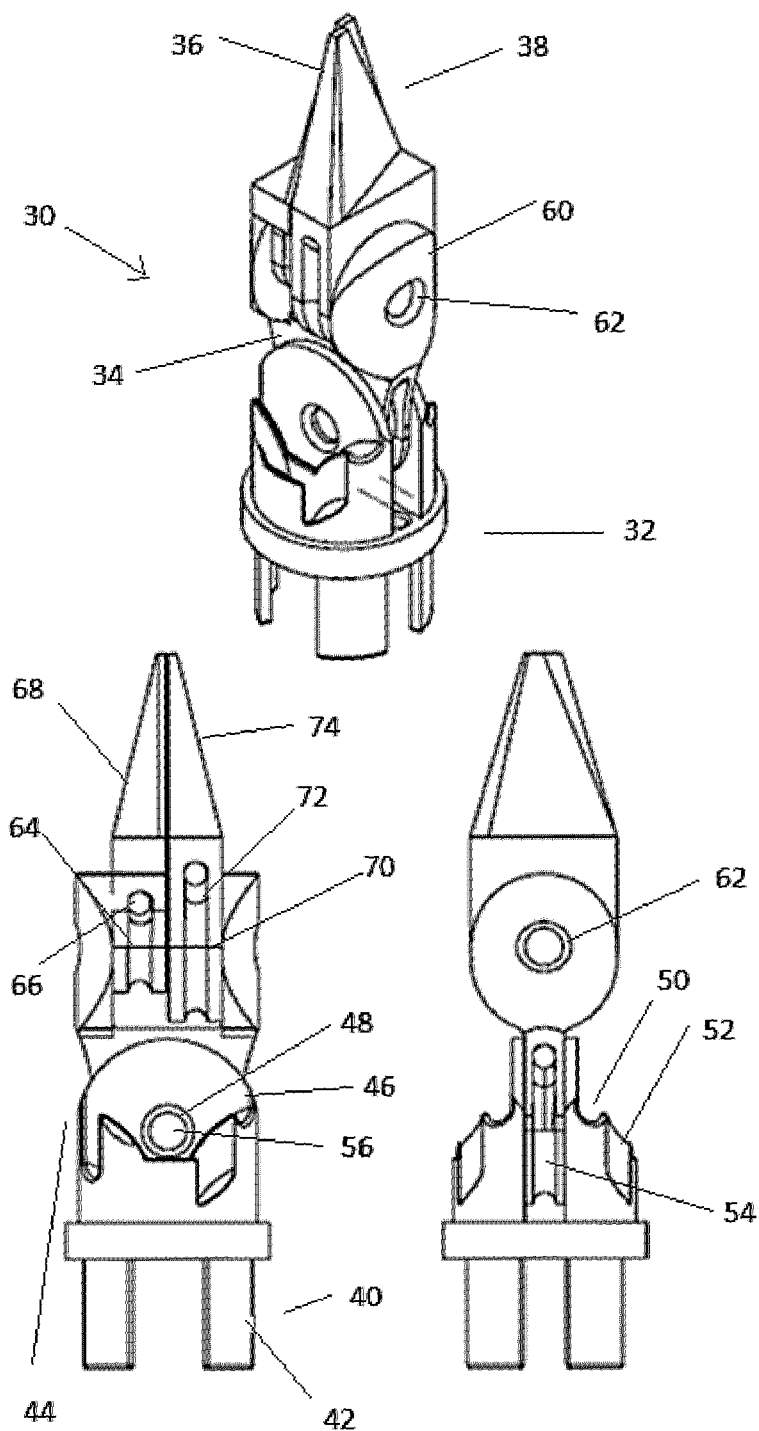
FIG. 3A is a multi-view drawing of an embodiment of the wrist mechanism having four cable guide channels per side.

An embodiment of the surgical tool 30 of the present disclosure is shown in detail in FIG. 3A. Specifically FIG. 3A shows an assembly comprising a first link 32, a second link 34, a first end-effector link 36 and a second end effector link 38.

The first link 32 has a cable guide attachment end 40 which allows the first link 32 to be connectable to a cable guide that protects the joint actuation cables which pass from an actuator to the surgical tool 30. In the present embodiment, the cable guide attachment end 40 comprises four alignment features 42 which generally protrude from the cable guide attachment end 40 and restrict movement of the first link 32 when it is positioned within a compatibly sized circular hole on the cable guide. One skilled in the art will appreciate that the cable guide may be any feature or features which allow the first link to be connectable to a cable guide and restrict movement of the first link relative to the cable guide. The first link 32 also has a pitch joint end 44 which comprises two pivot joint restraining plates 46 which are generally planer an parallel to each other and wherein each of said restraining plates 46 have one pivot pin hole 48 which is located concentrically with the pivot joint axis 21. The pivot joint restraining plates 46 are positioned in the central axis of the first link 32 such that a portion of the second link may be fitted through the space between the two plates 46 such that the second link can be actuated about the first link. The first link 32 has two inner guide channels 50 and two outer guide channels 52 where one inner guide channel 50 is positioned beside each of the two plates 46 on the side that is opposite to the central axis of the first link 32. Each of the outer guide channels 52 is positioned on the outside of the inner guide channels 50.

In the present embodiment of the first link 32 each of the inner 50 and outer 52 guide channels have two generally opposed guide arcs. In a further embodiment of the first link 32 one of the two opposed arcs is a large radius guide arc 51 and the other of the two opposed arcs is a small radius guide arc 53.

Figure 5A:
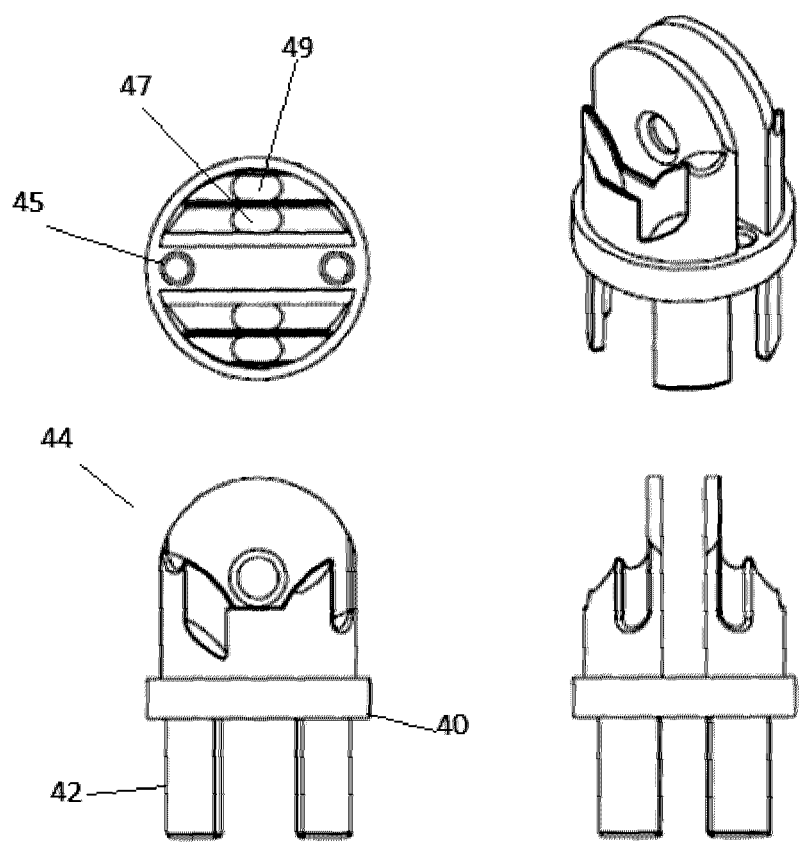
FIG. 5A is a multi-view drawing of an embodiment of the first link having four cable guide channels per side.

FIG. 5A shows the present embodiment of the first link 32 in detail. The first link 32 further has two pitch cable holes 45, one inner channel yaw cable hole 47 in each of the two inner guide channels 50 and one outer channel yaw cable hole 49 in each of the two outer guide channels 52. In the present embodiment, the pitch cable holes 45 are in the space between the two pitch joint restraining plates 46 and each pitch cable hole 45 is positioned on opposite sides of the roll axis 22, near the circumference of the first link 32. In the present embodiment, each inner channel yaw cable hole 47 is located in the nearest location to the roll axis 22 within the inner guide channel 50 and each outer channel yaw cable hole 49 is located in the nearest location to the roll axis 22 within the outer guide channel 52.

The second link 34 has a pivot plate 54 which is generally planer and its thickness is approximately equal to the space between the plates 46. The pivot plate 54 has a pivot pin hole 56 which is concentric with the pivot joint axis 21. The second link 34 also has a pivot cable coupling feature which allows a pivot cable to be coupled to the second link 34 such that the pivot cable can exert a torque on the second link 34. In the present embodiment, the pivot cable coupling feature is a pivot cable channel 58 which passes through the pivot plate 54. The pivot cable channel 58 is arc shaped and is concentric with the pivot pin hole 56. A pivot cable can be coupled to the second link 34 through the pivot cable channel 58. The second link 34 also has two yaw joint restraining plates 60 which each have one generally planer inside surface where each of the planer surfaces is parallel to each other. Each yaw joint restraining plate 60 has one yaw pin hole 62 each of which is aligned to be concentric with the yaw joint axis 23.

The first end-effector link 36 has a yaw plate 64 which is generally planer and its thickness is equal to approximately half of the thickness of the gap between the parallel surfaces of the yaw joint restraining plates 60. The yaw plate 64 has one yaw pin hole which is concentric with the yaw axis 23. The first-end effector link 36 has a first yaw cable coupling feature which allows a first yaw cable to be coupled to the first end-effector link 36 such that the first yaw cable can exert a torque on the first end-effector link 36. In the present embodiment the first yaw cable coupling feature is a first yaw cable channel 66 which passes through the yaw plate 64 and is concentric with the yaw axis 23. The first yaw cable channel 68 is circular and encircles the yaw pin hole such that a taught first yaw cable may pass around the first yaw cable channel 68 and the first yaw cable after passing through the channel 68 is offset from the end of the first yaw cable before passing through the channel 68 by the diameter of the circular channel 68. The first end-effector link 36 also has a tool end 68.

The second end-effector link 38 has a yaw plate 70 which is generally planer and its thickness is equal to approximately half of the thickness of the gap between the parallel surfaces of the yaw joint restraining plates 60. The yaw plate 70 has one yaw pin hole which is concentric with the yaw axis 23. The second-end effector link 38 has a second yaw cable coupling feature which allows a second yaw cable to be coupled to the second end-effector link 38 such that the second yaw cable can exert a torque on the second end-effector link 38. In the present embodiment the second yaw cable coupling feature is a second yaw cable channel 72 which passes through the yaw plate 70 and is concentric with the yaw axis 23. The second yaw cable channel 72 is circular and encircles the yaw pin hole such that a taught second yaw cable may pass around the second yaw cable channel 72 and the second yaw cable after passing through the channel 72 is offset from the end of the second yaw cable before passing through the channel 72 by the diameter of the circular channel 72. The second end-effector link 38 also has a tool end 74.

The pivot joint is formed by first link 32, second link 34 and a pivot joint pin where the pivot plate 54 is positioned between the two pivot joint restraining plates 46 and the pivot joint pin passes through the pivot pin holes 48 of the first link 32 and the pivot pin hole 56 of the second link 34 such that the second link 34 is rotatable about the pitch joint axis 21 relative to the first link 32. In the present embodiment, the pivot joint has 180° of rotational freedom about the pivot axis 21. However, one of ordinary skill in the art will appreciate that the surgical tool may be configured where the pivot joint has a different rotational freedom.

The yaw joint is formed by the second link 34, the first end-effector link 36, the second end-effector link 38 and a yaw joint pin where the yaw plates 64 and 70 are positioned between the two yaw joint restraining plates 60 and the yaw joint pin passes through the yaw pin holes 62, the yaw pin hole in plate 64 and the yaw pin hole in plate 70 such that each of the first end-effector link 36 and the second end-effector link is independently rotatably about the yaw axis 23 relative to the second link 34. In the present embodiment, the yaw joint has 180° of rotational freedom about the yaw axis 23. However, one of ordinary skill in the art will appreciate that the surgical tool may be configured where the yaw joint has a different rotational freedom.

The first end-effector link 36 and the second end effector link 38 may be rotated relative to each other about the yaw axis 23 which enables the end-effector links to perform tasks which require one member to rotate relative to another member. For example, the first 36 and second 38 end-effector links may be configured as forceps, needle drivers, retractors or scissors. One skilled in the art will appreciate that the end-effector links of the present disclosure may be configured as other tools which are compatible with the device of the disclosure.

In the present embodiment of the surgical tool 30, the diameter of the first yaw cable channel 66 is equal to the spacing between the two inner guide channels 50 such that one inner guide channel 50 guides a first yaw cable on one side of the first yaw cable channel 66 and the other inner guide channel 50 guides the first yaw cable on the other side of the first yaw cable channel 66. This means that the path of the first yaw cable between the first end-effector link 36 and the inner guide channels 50 will be parallel to the roll axis 22. The diameter of the second yaw cable channel 72 is equal to the spacing between the two outer guide channels 52 such that that one outer guide channel 52 guides a second yaw cable on one side of the second yaw cable channel 72 and the other outer guide channel 52 guides the second yaw cable on the other side of the second yaw cable channel 72. This means that the path of the second yaw cable between the second end-effector link 36 and the outer guide channels 52 will be parallel to the roll axis 22.

In an alternate embodiment of the surgical tool of the present disclosure, the surgical tool may have one end-effector link or more than two end-effector links and the surgical tool is similar to the surgical tool 30 but it is adapted for one or more than two yaw joint cables.

Figure 3B:
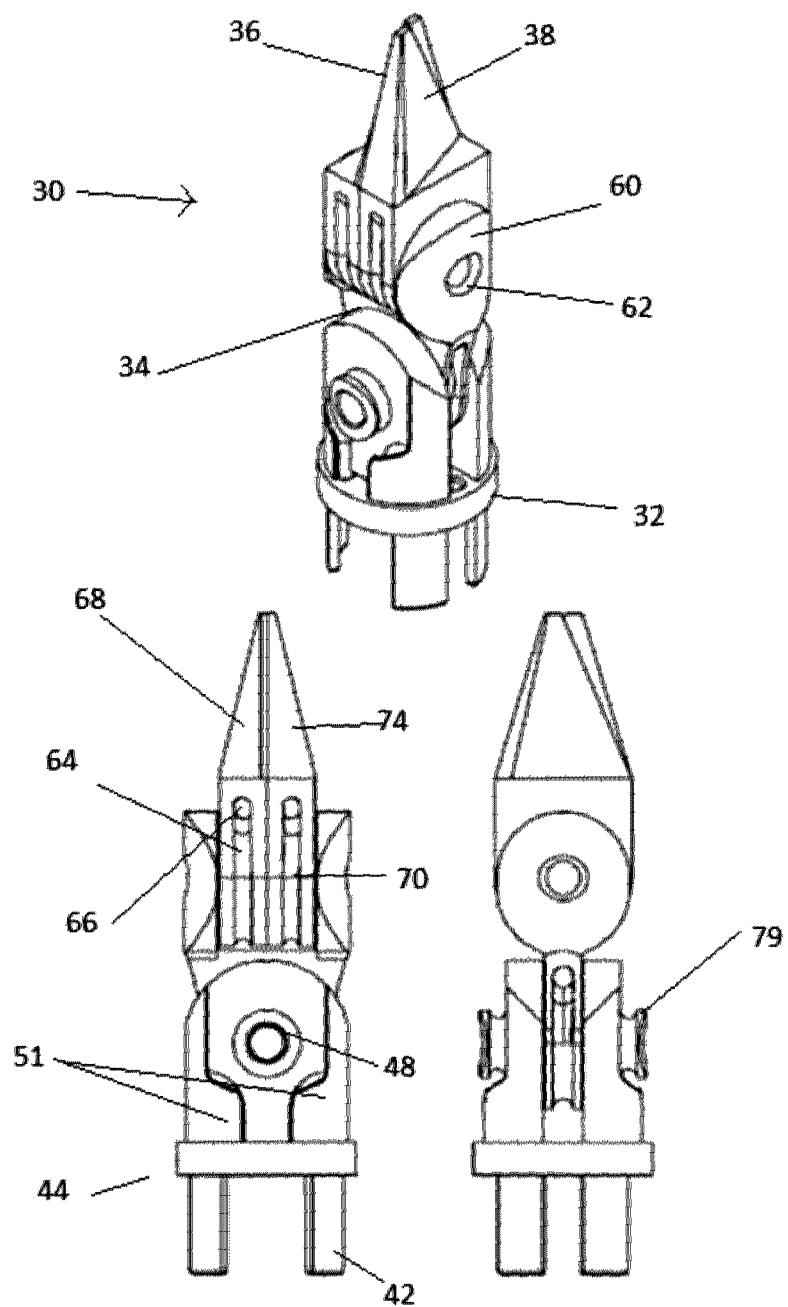
FIG. 3B is a multi-view drawing of an embodiment of the wrist mechanism having a circular cable guide channel and an outer cable guide channels.

A second embodiment of the surgical tool 30 of the present disclosure is shown in FIG. 3B. Specifically FIG. 3B shows an assembly comprising a first link 32, a second link 34, a first end-effector link 36 and a second end effector link 38.

In the present embodiment, each side of the cable guide attachment end 40 generally comprises four alignment features which generally protrude from the cable guide attachment end 40 and restrict movement of the first link 32 when it is positioned within a compatibly sized circular hole on the cable guide. The first link 32 also has a pitch joint end 44 which comprises two pivot joint restraining plates 46 which are generally planer an parallel to each other and wherein each of said restraining plates 46 have one pivot pin hole 48 which is located concentrically with the pivot joint axis 21. The pivot joint restraining plates 46 are positioned in the central axis of the first link 32 passes through the space between the two plates 46.

Each side of the first link 32 has two opposed guide channels where one of the opposing guide channels 51 is positioned beside each of the two plates 46 on the side that is opposite to the central axis of the first link 32. Both sides of the first link further comprise an additional guide protrusion 79 which is located between the axis of the pitch joint pin and the end of the first link 32.

In the present embodiment of the first link 32 each of the opposed guide channels 51 is an arced guide and the guide protrusion 79 is cylindrical in shape and concentric to the axis of the pitch joint pin. The guide protrusion may also be asymmetrical in form and may be located anywhere in a range between the pitch pin joint and then end of the first link. In this embodiment of the tool, the yaw guide cables are strung along the first link and second link to connections at the end effectors.

Figure 5B:
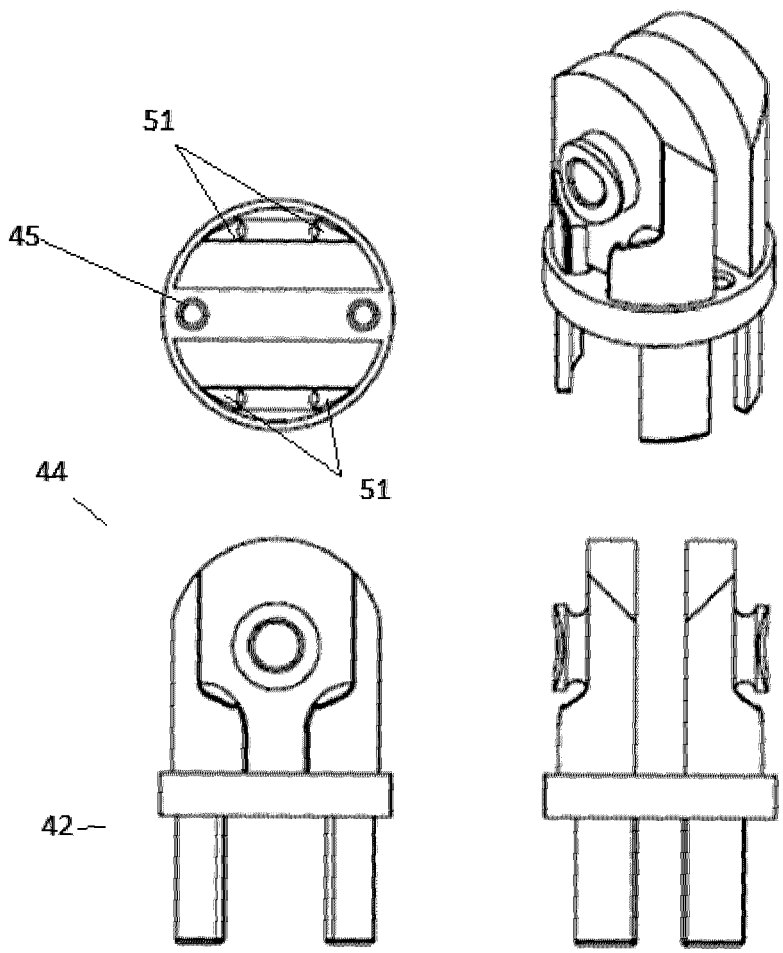
FIG. 5B is a multi-view drawing of an embodiment of the first link having a circular cable guide channel and outer cable guide channels.
Figure 6A:
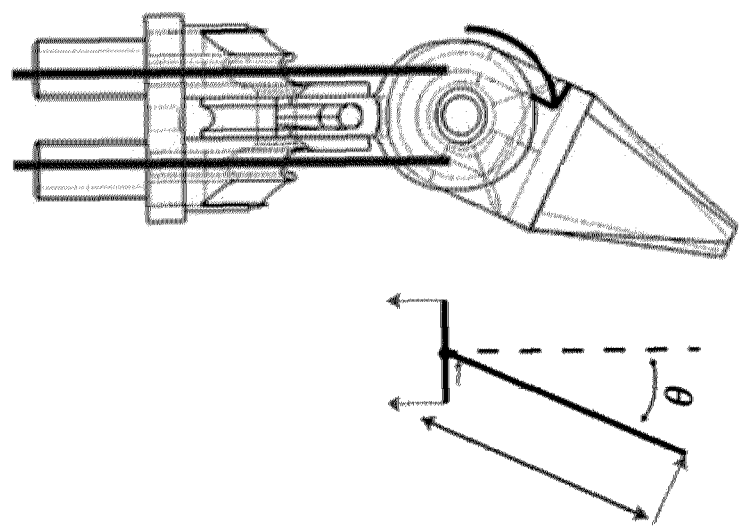
FIG. 6A is a schematic of an embodiment of the first link rotating about the pitch axis and the tangent angle of the cable due to this rotation.
Figure 6B:
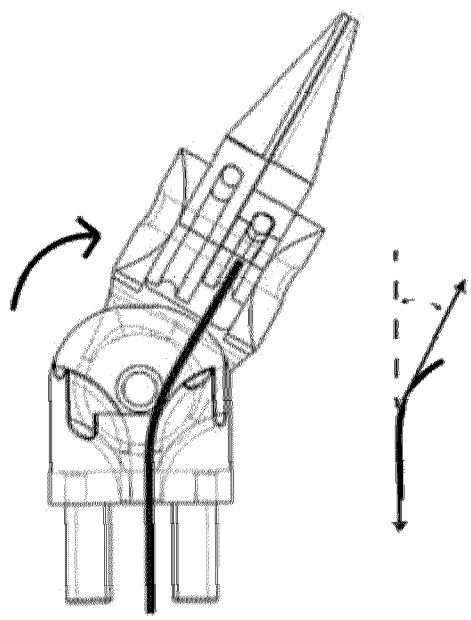
FIG. 6B is a schematic of an embodiment of the first link rotating about the yaw axis and the tangent angle of the cable due to this rotation.

FIG. 5B shows the present embodiment of the first link 32 in detail. The first link 32 further has two pitch cable holes 45 and two inner guide arcs 51. In the present embodiment, the pitch cable holes 45 are in the space between the two pitch joint restraining plates 46 and each pitch cable hole 45 is positioned on opposite sides of the roll axis 22, near the circumference of the first link 32.

As eluded to in the previous discussion of alternative embodiments, the second link 34 has a pivot plate 54 which is generally planer and its thickness is approximately equal to the space between the plates 46. The pivot cable coupling feature is a pivot cable channel 58 which passes through the pivot plate 54. The pivot cable channel 58 is arc shaped and is concentric with the pivot pin hole 56. A pivot cable can be coupled to the second link 34 through the pivot cable channel 58.

In the present embodiment, the second link 34 also has two yaw joint restraining plates 60 which each have one generally planer inside surface where each of the planer surfaces is parallel to each other. The pivot joint is formed by first link 32, second link 34, a pivot joint pin, pivot plate 54 and two pivot joint restraining plates 46. Likewise, the yaw axis is comprises of the second link 34, the first end-effector link 36, the second end-effector link 38 and a yaw joint pin where the yaw plates 64 and 70 are positioned between the two yaw joint restraining plates 60 and the yaw joint pin passes through the yaw pin holes 62, the yaw pin hole in plate 64 and the yaw pin hole in plate 70 such that each of the first and second end-effector links are independently rotatably about the yaw axis 23 relative to the second link 34.

In the present embodiment, the first end-effector link 36 has a yaw plate 64 which is generally planer and its thickness is equal to approximately half of the thickness of the gap between the parallel surfaces of the yaw joint restraining plates 60. The yaw plate 64 has one yaw pin hole which is concentric with the yaw axis 23. The first-end effector link 36 has a first yaw cable coupling feature which allows a first yaw cable to be coupled to the first end-effector link 36 such that the first yaw cable can exert a torque on the first end-effector link 36. In the present embodiment the first yaw cable coupling feature is a first yaw cable channel 66 which passes through the yaw plate 64 and is concentric with the yaw axis 23. The first yaw cable channel 68 is circular and encircles the yaw pin hole such that a taught first yaw cable may pass around the first yaw cable channel 68.

In the present embodiment, the guide protrusion functions to direct the yaw cables during pitch motion of the wrist whereby the yaw cable on the opposing side to the direction of the pitch motion wraps around the guide protrusion. The wrapping of the opposing yaw cable reduces the unbalanced moments experienced by the second link and end effectors during pitching motion. The wrapping of the yaw cable also reduces the magnitude of the cable path length change, reducing the amount of slack introduced into that cables which would otherwise have to be compensated for.

The second end-effector link 38 has a yaw plate 70 which is generally planer and its thickness is equal to approximately half of the thickness of the gap between the parallel surfaces of the yaw joint restraining plates 60. The yaw plate 70 has one yaw pin hole which is concentric with the yaw axis 23. The second-end effector link 38 has a second yaw cable coupling feature which allows a second yaw cable to be coupled to the second end-effector link 38 such that the second yaw cable can exert a torque on the second end-effector link 38.

Figure 3C:
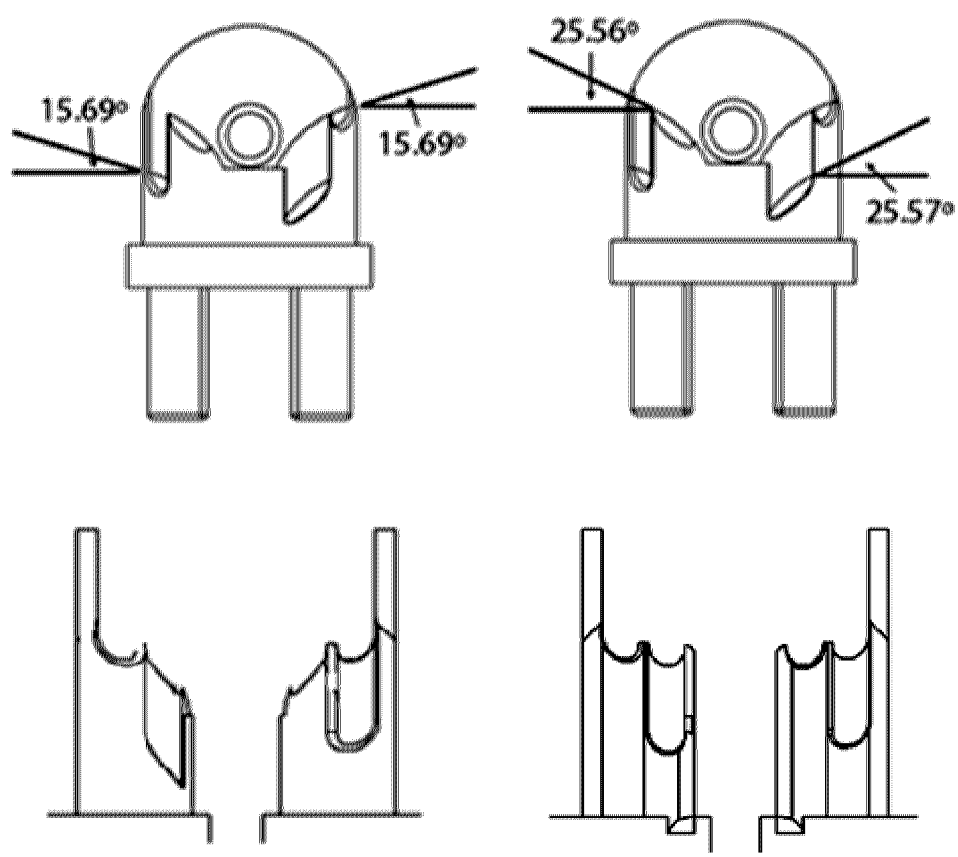
FIG. 3C is a multi-view drawing of an embodiment of the first link of the wrist mechanism showing the angles of the guide channels curves and groove of the inner and outer channels.

The preferred minimum tangent angle of each of the opposed guide arcs of the inner guide channel 50 is dependent on the diameter of first yaw cable channel 64 and the axial distance between the first yaw cable channel 64 and the center of the yaw joint pin. The minimum tangent angle is the minimum angle of a tangent to one of the guide arcs with respect to the horizontal axis. FIG. 3C shows the minimum tangent angles of the guide arcs of the first link 32. Where the minimum tangent angle for the guide arcs of the inner guide channel 50 is 15.69° and the minimum tangent angle for the guide arcs of the outer guide channel 52 is 25.57°.

Figure 4A:
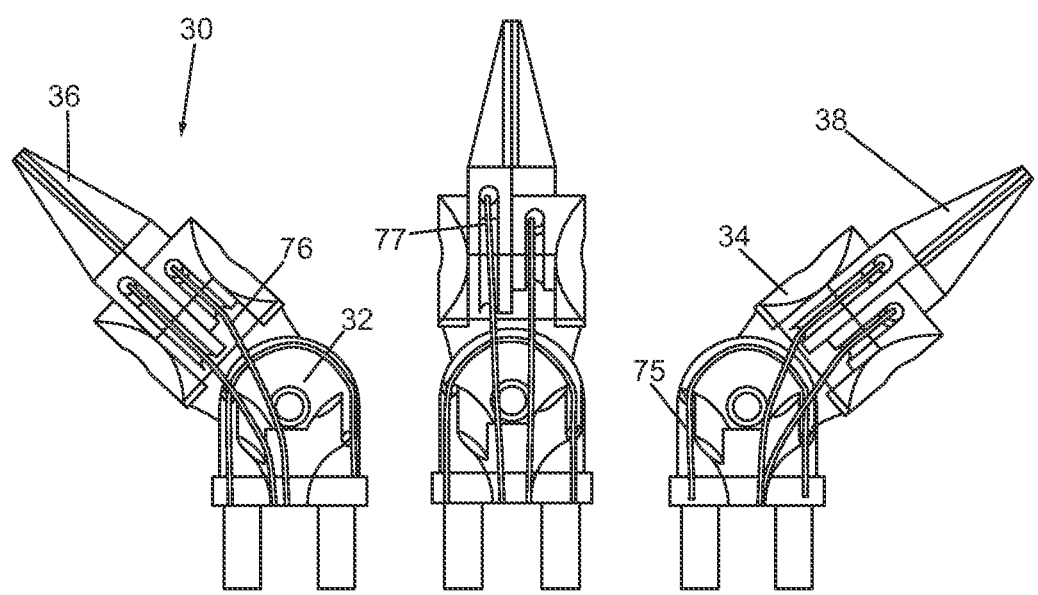
FIG. 4A is a diagram showing the cables attached to an embodiment of the wrist mechanism, and the change in cable circuit path length about the pitch axis.

FIG. 4A shows the surgical tool 30 where a pivot cable 75 is coupled to the pivot cable channel 58, a first yaw cable 76 is coupled to the yaw cable channel 66 and a second yaw cable 77 is coupled to the yaw cable channel 72. Specifically, FIG. 4A shows how the pitch cable 75 exerts a torque on the second link 34 which causes the second link 34 to rotate about the pitch axis 21 relative to the first link 32. This motion causes the path length of both the first yaw cable 76 and second yaw cable 77 to change. The change in path length is a result of the each inner guide channel 50 increasing the path length of the first yaw cable 76 between the inner channel yaw cable hole 47 and the first yaw cable channel 66, and each outer guide channel 52 increasing the path length of the second yaw cable 77 between the outer channel yaw cable hole 49 and the second yaw cable channel 72. The guide channels 50 and 52 are configured to increase the path length of the yaw cables 76 and 77 to maintain tension in the yaw cables 76 and 77 which prevents the surgical tool 30 from undergoing any sort of snapping motion. A snapping motion is caused when an object experiences a sudden torque. The present embodiment of the surgical tool 30 prevents snapping motion due to the arc guides 51 and 53 which ensure that the first 76 and second 77 yaw cables are tangent to the arc guides 51 and 53.

Figure 4B:
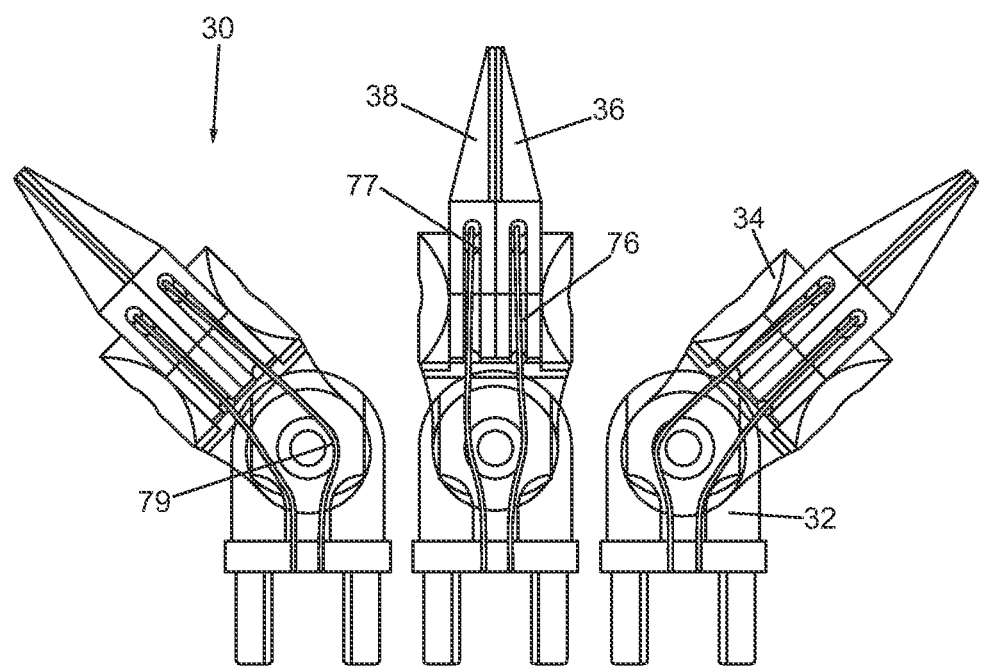
FIG. 4B is a diagram showing the cables attached to an alternative embodiment of the wrist mechanism, and the change in cable circuit path length.

Referring to FIG. 4B, the embodiment of the proposed surgical tool is shown where the first link comprises a pair of opposing arced guides and a cylindrical guide protrusion for guiding the yaw cables. In the present embodiment, the cylindrical guide protrusion is placed concentric to the pitch join pin. The previously described wrapping of the opposing yaw cable about the guide protrusion is also displayed. A first yaw cable 76 is coupled to one of the opposing arced guides and the guide protrusion 79 and a second yaw cable 77 is coupled to the guide protrusion and the other of the opposing arced guides. FIG. 4B further displays the pitch cable 75 exerting a torque on the second link 34 and causing the second link 34 to rotate about the pitch axis 21 relative to the first link 32. This motion causes the path length of both the first yaw cable 76 and second yaw cable 77 to change and one of the first yaw cable 76 or second yaw cable 77 (whichever cable is on the opposite side to the direction of pitch motion) to wrap around the guide protrusion.

Figure 7A:
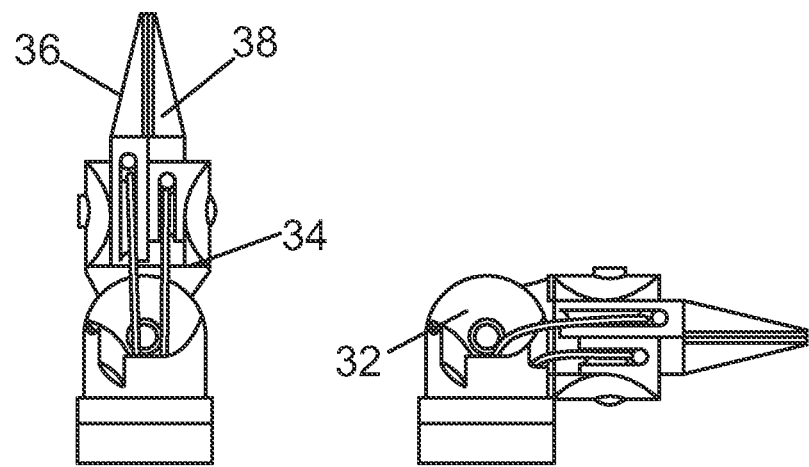
FIG. 7A is a pitch axis view of a 3D printed in 17-4PH stainless steel model of the wrist mechanism with routed cables.
Figure 7B:
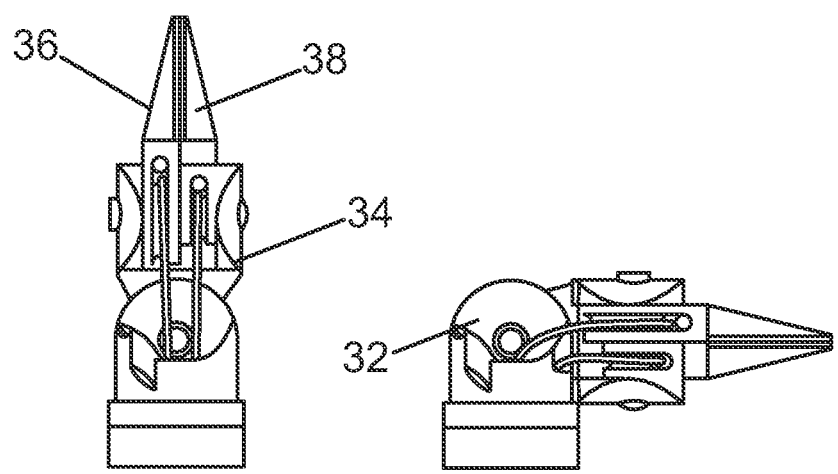
FIG. 7B is a yaw axis view of a 3D printed in 17-4PH stainless steel model of the wrist mechanism with routed cables.

FIG. 7A displays a complete fabricated surgical tool being three-dimensionally (3D) printed using direct metal laser sintering (DMLS) in 17-4PH stainless steel at 5 mm diameter. This is merely an exemplary method of manufacturing the links and structure of the compact surgical tool. The new surgical tool has fewer components as well as a smaller length (4 components and a length of 5 mm) and more compact workspace (as shown in FIG. 1D) when compared to the existing wrist tool instruments. Length is defined as the distance from the pitch to yaw axis as shown in FIG. 1A-1D as the size of the grippers can vary. The number of components excludes cables and cable fittings.

Figure 8A:
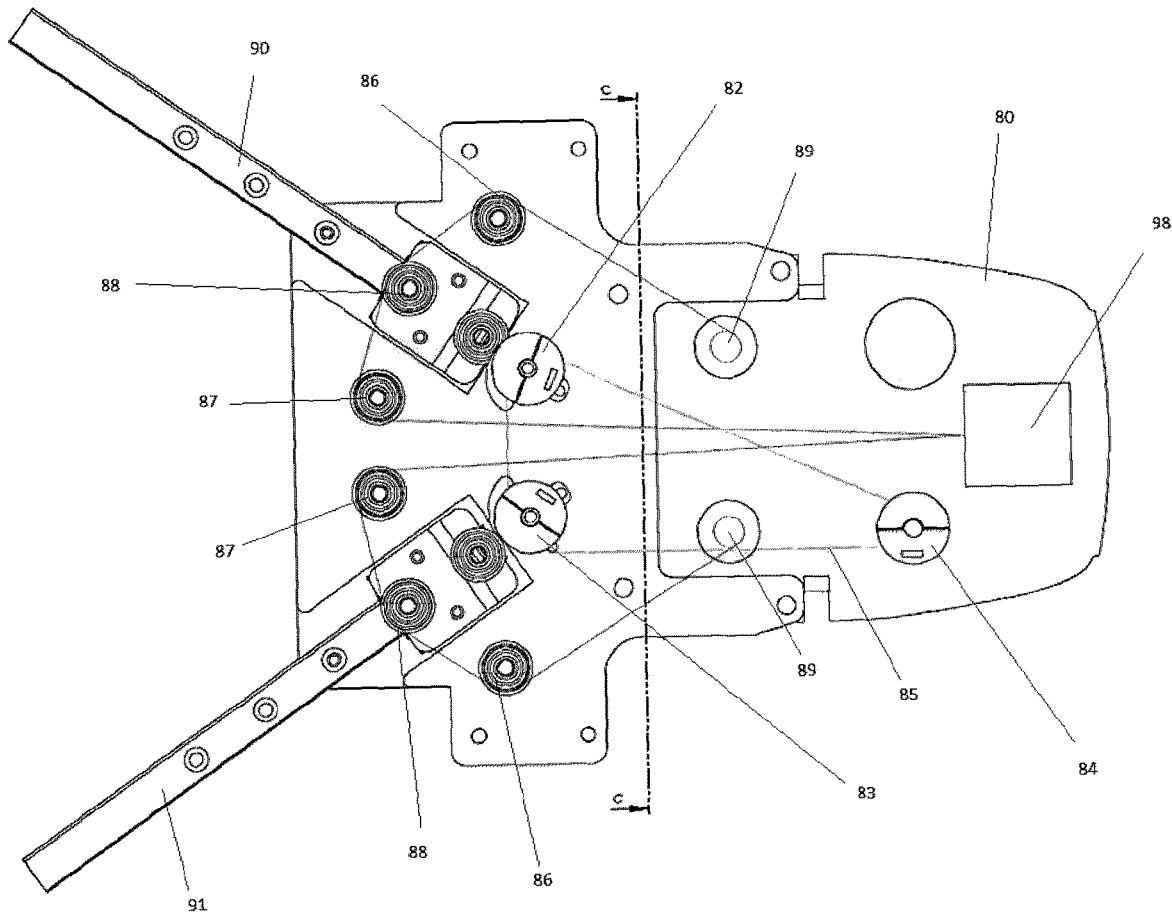
FIG. 8A is a top view of the tensioning actuation mechanism.
Figure 8B:
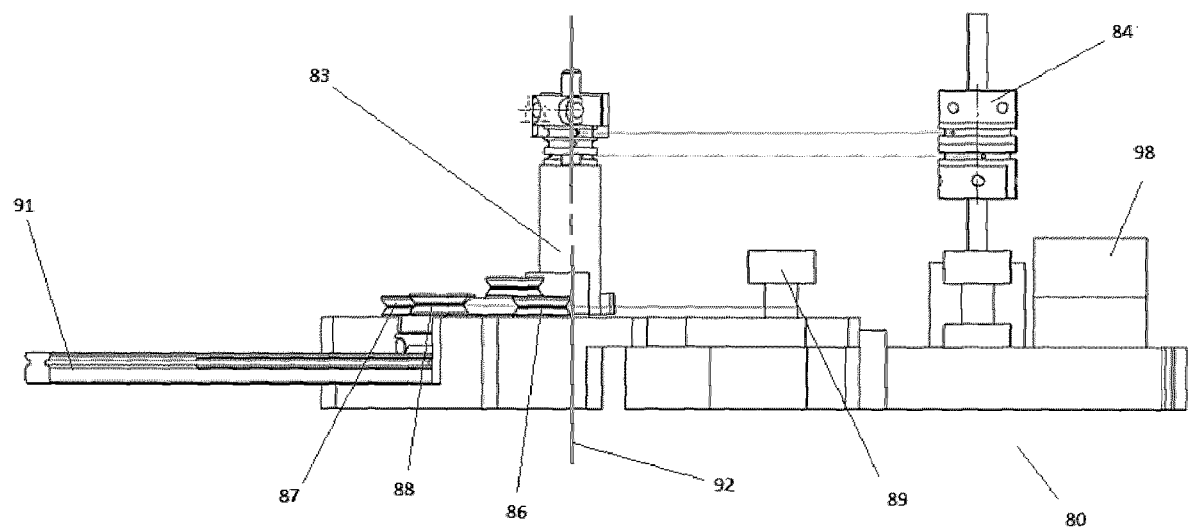
FIG. 8B is a side view of the tensioning actuation mechanism.

An additional challenge to the surgical tool design is the cable circuit path length change that occurs while the tool pitches about the pitch joint pin. As the tool pitches, a mechanism is required to ensure that cable tension is maintained to consistently and effectively actuate the grippers and provide yaw motion. A tensioning mechanism with integrated cam devices may be configured for use with the proposed tool to confirm constant cable tension during pitch motion to provide accurate control for yaw motion. FIGS. 8A and 8B show a top view and a side view of the tensioning mechanism 80 in accordance with an embodiment of the invention predominantly employing pulleys and cams to control the tool articulation, cable tension and cable slack. The illustrated embodiment of the tensioning mechanism 80 includes a roll motion driver 98, two cam mechanisms 82, 83, two yaw guide cables, a cam guide cable 85, first and second pulleys 86, 87 for each yaw guide cable and a tensioning pulley 88 for each yaw guide cable. The tensioning mechanism further comprises a pitch driver 84; two sliding mounts or linear actuating elements in channels 90, 91 and a yaw driver for each of the guide cables 89. A system of first and second pulleys 86, 87 and the tensioning pulley 88 is integrated with each of the yaw guide cables, the linear actuating element and the yaw drive for providing tension control (to reduce slack) for each yaw guide cable. The components 86, 87, 88, 90 and 91 can be made of any suitably durable material such as machined plastic or metal depending on the required loads and tolerances of the individual components.

In the same embodiment of the tensioning mechanism, each tensioning pulley 88 is spaced between the first and second pulleys 86, 87. Each of the yaw cables is wrapped around one of the first pulleys 86, and is further wrapped around the tensioning pulley 88 and second pulley 87 and is workably attached to a yaw driver 89. The tensioning pulley 88 is generally movable relative to the first and second pulleys 86, 87 to facilitate changing of cable lengths for maintaining cable tension in the cable between the second pulley and the surgical tool. The movement of each tensioning pulley 88 is generally achieved by a tensioning device which moves the tensioning pulley relative to the other pulleys in a manner such that the length of the yaw cable disposed between the first and second pulleys changes as a result of a positional change of the tensioning pulley.

In a preferred embodiment of the tensioning mechanisms, each of the tensioning pulleys 88 are attached to a tensioning device which is the linear actuating elements 90, 91 disposed within a linear channel. Linear movement of the linear actuating elements 90, 91 connected to each of the tensioning pulleys will results in a corresponding linear movement of the tensioning pulleys 88 relative to the first and second pulleys 86, 87. This linear movement will further cause in a change in the length of the yaw cable disposed between the first and second pulleys 86, 87, thus altering tension within the yaw cables and picking up slack of the yaw cable due to tool pitching.

The above noted linear motion of the sliding mounts or linear actuating elements within their channels (and corresponding movement of the tensioning pulleys) is generally induced by the two cam mechanisms 82, 83, workably connected to each the sliding mounts or linear actuating elements 90, 91. The use of cam mechanisms generally reduces the amount of pre-tensioning required for the tensioning mechanism and allows higher force generation capacity within the tensioning mechanism. Referring to FIG. 8B and FIG. 9B, the two cam mechanisms 82, 83 are capable of rotating about a cam axis 92 where rotation of the cam about the cam axis generally controls the linear position of the slide mount and tensioning pulley. The motion of the two cam mechanisms is coupled to motion of wrist pitch through a cable which is connected to the pitch driver 84. As the pitch driver 84 rotates, the two cam mechanisms 82, 83 rotate, contacting the linear actuating elements 90, 91.

The cam shape is generally oblique and is determined by the cable circuit path discrepancy that occurs as the surgical tool moves or pitches about the pitch axis. As the two cam mechanisms rotate about the cam axis, the oblique shape of the cam contacts the sliding mount or linear actuating element and causes a deviation of the linear actuating element away from the cam axis. The extent of the deviation of the linear actuating element from the cam axis is dependent on the direction and the degree of cam rotation. The deviation of the linear actuating element controls yaw cable tension as follows: when the element is actuated, the tensioning pulley attached to the linear actuating element also deviates from the cam axis, causing an increase in the length of yaw cable disposed between the first and second pulley and a decreases when the linear actuating element moves towards the cam axis.

Figure 10:
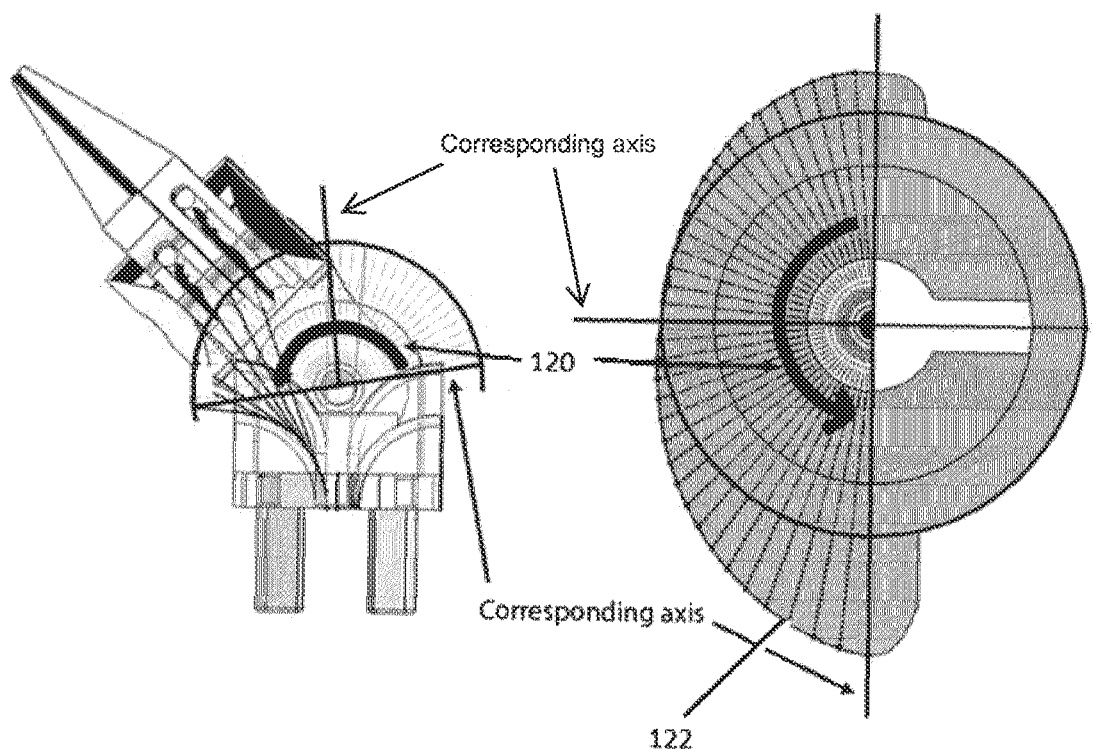
FIG. 10 is a diagram of the cable path length change as the wrist pitches and the corresponding CAM with dimensions that match cable path length change.

The dimensions and oblique cam perimeter shape of the two cam mechanisms are coupled to the pitch cable by a coupling system such that the length of said at least one yaw cable between said first pulley and said second pulley changes with respect to the angle between said first link and said second link. In an embodiment shown in FIG. 10, the cable circuit path discrepancy at 5° intervals of wrist pitch 120 are used to create an oblique cam perimeter shape 122 at the corresponding 5° angles. As the second link pitches about the first link, the two cam mechanisms partially account for the changing cable slack. The coupling of the cam dimensions and oblique configuration to the pitch cable ensures that the cam mechanisms are configured with oblique outer perimeter dimensions that increase or decrease in exact accordance with any yaw cable path length change as the wrist pitches. The two cam mechanisms 86, 87 may be coupled to pulleys and positioned such that they are in direct contact with the pitch cable. This particular configuration of the cam mechanisms limits the introduction of additional friction surfaces as the pitch cable cables passes over the cam mechanisms.

Figure 13:
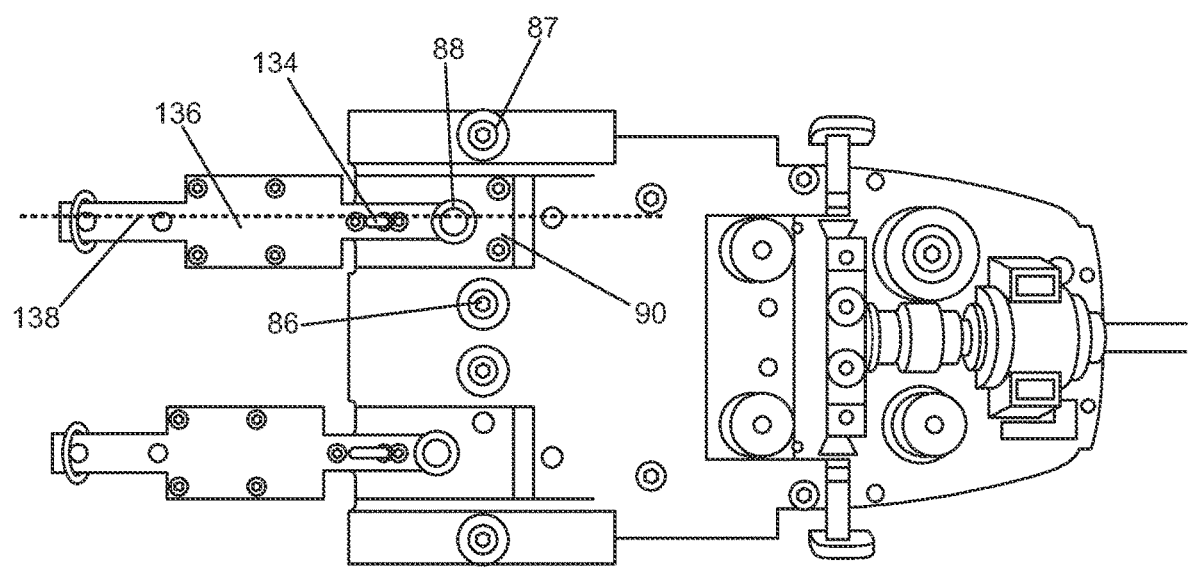
FIG. 13 is a top view of a tensioning actuation mechanism with a rail and car linear actuation system.

Referring to FIG. 13 an alternative embodiment of the tensioning device and the linear actuating element is provided comprising at least one rail feature 134 and a car 136 connectable to said tensioning pulley 88 such that said car is slidable along one axis 138 relative to said at least one rail. The linear actuating element may further be configured as a spring slide mechanism having a spring being connected at one end to the linear actuating element 90 and being connected at the other end to a fixed feature such that the length of the yaw cable between said first pulley 86 and said second pulley 87 decreases when the tension in said at least one yaw cable decreases. Similar to the cam mechanism, a consistent method of providing appropriate cable tension is achieved by the rail car or slide spring mechanisms. Adding the rail car or spring in series, which is connected to the linear actuating element and the yaw cables, is beneficial as it accounts for changing cable circuit lengths during wrist pitch. This mechanism is configured such that the spring tension is always greater than the maximum cable tension that might be encountered during a procedure to ensure that the wrist is non-compliant. For this mechanism, it may be beneficial to have a second spring element or rail car which can be manually positioned to increase the tension in the cables and a first rail car which moves accordingly, adjusting the cable tension during wrist pitch. The spring in series may be a spring that is pre-tensioned such that any external force on the wrist does not move the spring ensuring the wrist is non-compliant.

Figure 9A:
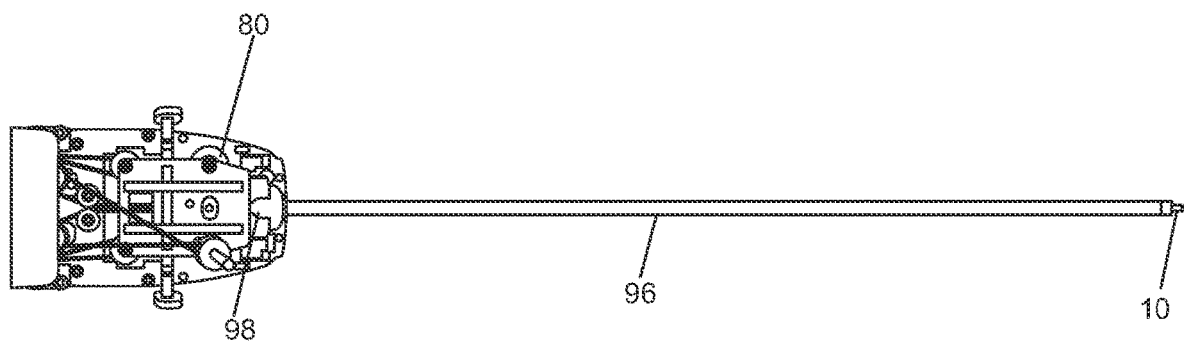
FIG. 9A is a top view of tensioning actuation mechanism integrated with a laparoscopic, surgical shaft for distal placement of the wrist mechanism.
Figure 9B:
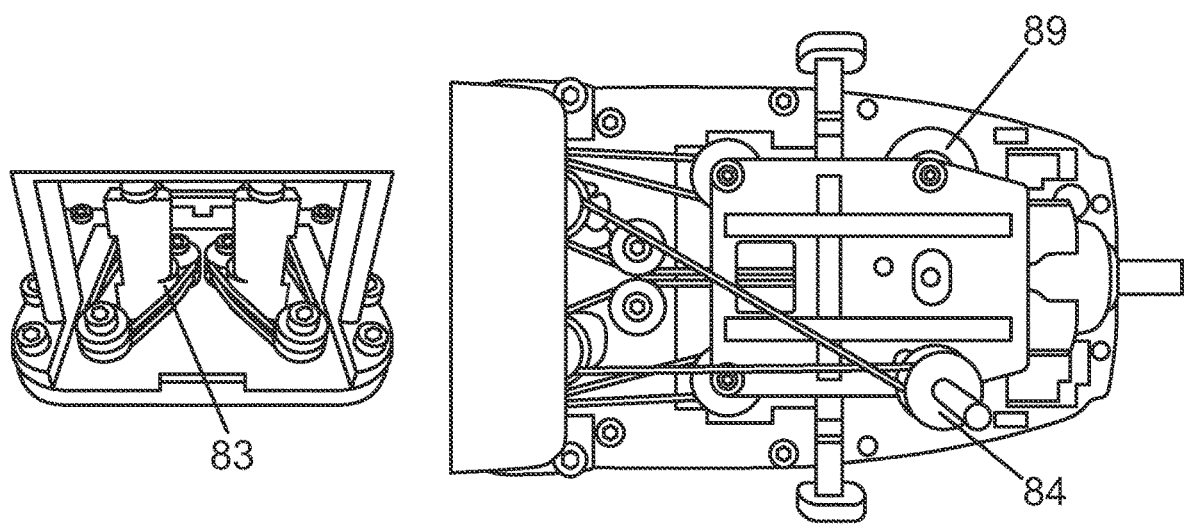
FIG. 9B is a top view of spring tensioning actuation mechanism and CAM tension control system.

Referring to FIG. 9A, the integration of the tensioning mechanism and surgical tool is shown generally. The setup of an exemplary surgical procedure includes the tensioning mechanism 80, a shaft 96 extending from the tensioning mechanism 80, and the surgical tool 30 attached via the first link at the distal end of the shaft 96. The yaw and pitch cables may be threaded and extended through the shaft 96 to connect between the surgical tool 30 and the tensioning mechanism 80. In the same setup shown in FIG. 9A, the shaft, which is extended from the tensioning mechanism, is hollow and houses the pitch and yaw cables. The shaft is rotatably attached to a driver 98 on the tensioning mechanism 80 such that the shaft 96 can be rotated about its own axis to achieve roll motion of the surgical tool 30. The shaft is preferably rigid, but a flexible shaft configuration may also be implemented for use in procedures requiring insertion of the shaft through an endoscope or other curved, guiding feature.

In an additional embodiment, the surgical tool attached to the distal end of the shaft has a 5 mm working radius such that the distance between the tip of the end effector and the pitch joint pin is 5 mm.

Figure 11:
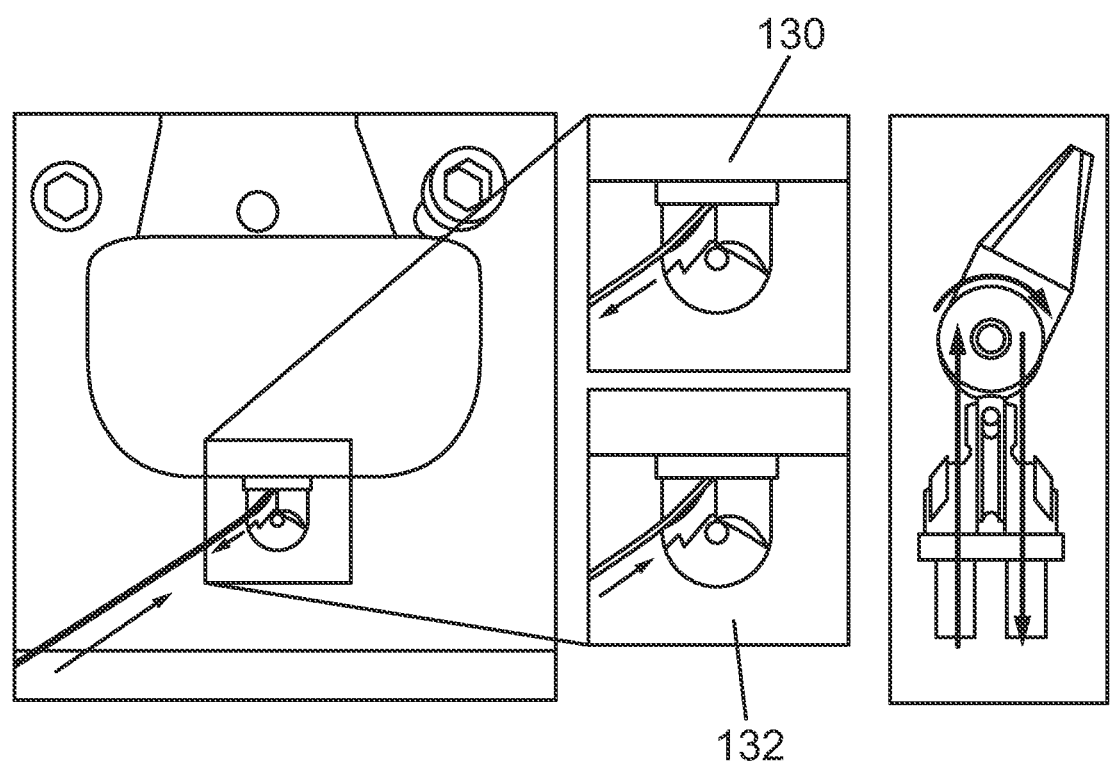
FIG. 11 is a diagram of the cable moving along the link guide channels illustrating the direction of movement for cable pulling and cable pushing.

Referring to FIG. 11 a diagram of a yaw cable moving along the link guide channels is provided, illustrating the direction of movement for cable pulling 130 and cable pushing 132. Elevated and consistent cable tension is achieved through movement of the cable proximally in relation to the first link. This is the direction of interest as movement of the grippers is through a pulling motion as opposed to a pushing which is unfavorable using flexible cables. This motivates the use of multiple yaw cables, such as those seen in FIG. 4A to achieve a full range of yaw motion and synchronized and unsynchronized motion of two end effectors without the use of a "pushing" motion of one of the cables. In addition, it is during the pulling (movement of the cables from distal to proximal) that the highest normal forces of the cable along the guide channels occur and this corresponds to the highest friction forces. In addition, the direction of pull results in a more unfavourable interaction between the outer perimeter edge of the guide channel and the cable itself results in higher friction forces. The presence of the elevated friction forces along the guide channel grooves and at the perimeter edge of the guides motivates the use of arced guides with a lower perimeter angle and the use of smoother guide cables.

For the proposed device, it is desirable to have a guide cable material such that the contact between the guide groove channels and the pitch/yaw guide cables has a low coefficient of friction, but still has a relatively high tensile strength (i.e. smoother steels). The pitch cable and at least one yaw cable are generally made of a solid, low friction metal such as stainless steel, CNC milled steel, nylon coated stainless steel or polytetrafluoroethylene coated stainless steel.

Figure 12A:
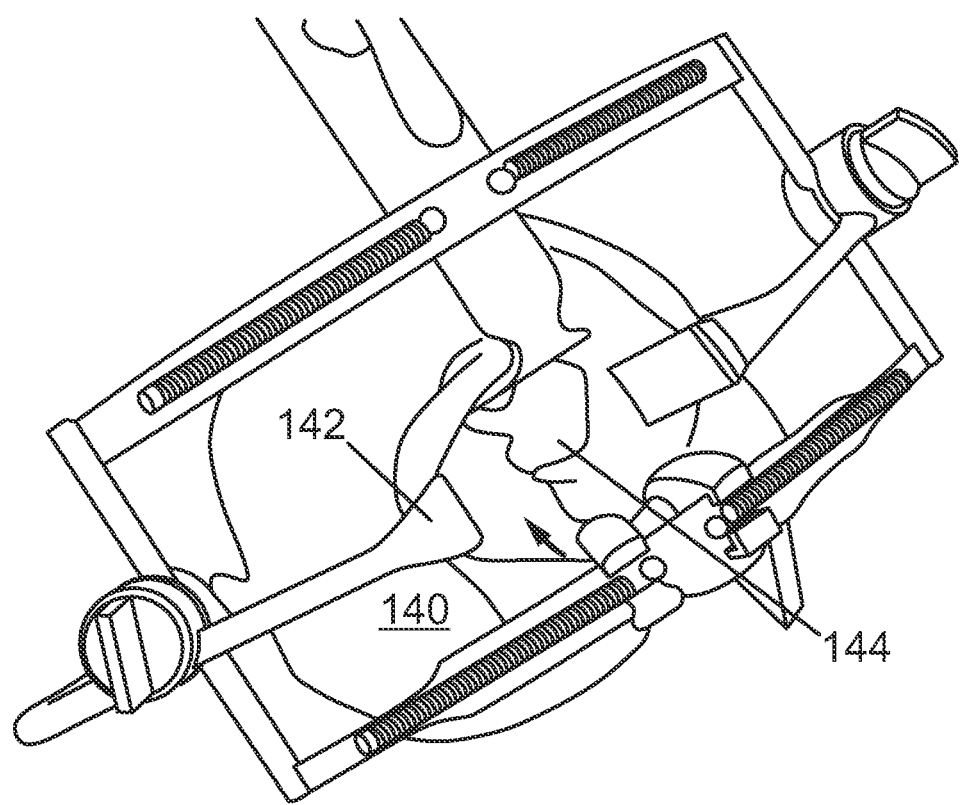
FIG. 12A is a diagram of a typical setup for performing a cleft palate surgical procedure.
Figure 12C:
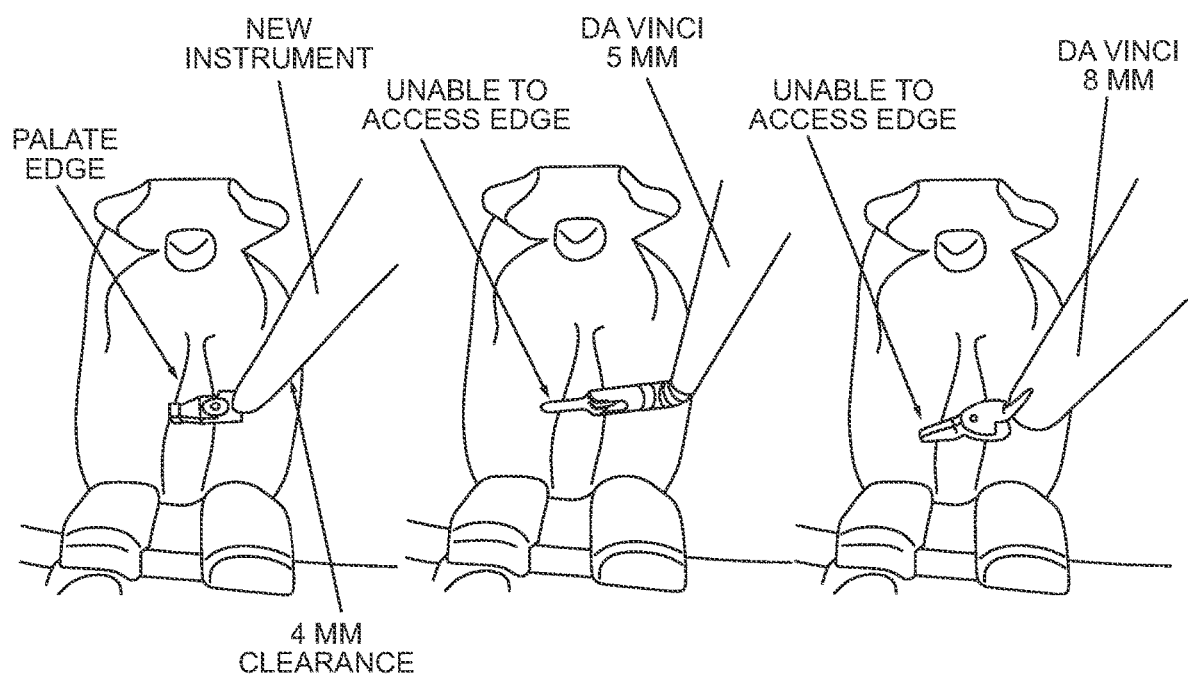
FIG. 12C is a comparison of clearance in a typical cleft palate setup of the new wrist mechanism and (d) 5 mm and (e) 8 mm da Vinci™ instruments.

The proposed tool is generally integrated with a surgical robot system which includes a tensioning and actuation mechanisms such as those described previously and show in FIGS. 8A, 8B and 9B. The proposed tool is also generally integrated with a shaft extending from the tensioning mechanism as show in FIG. 9A. Referring to FIG. 12A-C the integration of the proposed tool 30 with a surgical robot system 146 and the placement of the tool within the oral cavity 144 of a validated cleft palate phantom 140 with surgical spacers 142 is shown. The introduction of the surgical tool into the phantom enables assessment of the clearance of the instrument shaft to the oral aperture compared to the existing da Vinci™ 5 and 8 mm EndoWrist instruments as presented in FIG. 1. Greater clearance while accessing important anatomical structures results in fewer instrument collisions during a cleft palate procedure. A minimum of six degrees of freedom (DOF) (three position and three orientation) is required to optimally perform cleft palate surgery. The da Vinci™ provides the required articulation within the mouth and the necessary six DOF (three DOF from the external surgical control unit, four DOF at the wrist (pitch, yaw, roll, grip)) to perform cleft palate surgery.

Given the unique and complex shape of the palate, certain aspects of the cleft palate procedure are challenging using existing devices which generally have limited reachability and manipulability. The proposed tool helps to alleviate frequent collisions between an instrument and oral aperture. Critical steps of a cleft palate repair are feasible with reduced collisions using the proposed tool. Referring to FIG. 12C, it is apparent that the proposed surgical tool provides increased clearance between the instrument shaft containing the surgical tool and an oral cavity. The inability of the existing da Vinci™ instruments to access the edge of the palate without contacting the mouth can also be seen. Many of the above described embodiments can reduce the cost of minimally invasive surgical tools by reducing part numbers in the tool; the complexity of the tool or instruments; the cost of the materials used; the manufacturing complexity of the tool components and the difficulty of the assembly of the tool.

While the teachings described herein are in conjunction with various embodiments for illustrative purposes, it is not intended that these teachings be limited to such embodiments. On the contrary, the teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. A surgical tool for compact articulating during surgical procedures comprising:
   a pitch cable;
   at least one yaw cable;
   a first link having a pitch joint end with a pitch joint pin and at least one yaw cable guide channel;
   a second link having a yaw joint end with a yaw joint pin, said second link being rotatably connected to the pitch joint pin of the first link, said pitch cable being coupled to said second link such that said pitch cable can actuate said second link about said pitch joint pin;
   at least one end-effector link being rotatably connected to said yaw joint pin wherein the at least one yaw cable is coupled to said at least one end-effector link such that said at least one yaw cable can actuate said at least one end-effector link about said yaw joint pin;
   said at least one yaw cable guide channel being configured such that said at least one yaw cable travels through a smooth trajectory to said at least one end-effector link for any angle between said first link and said second link; and
   at least one tensioning mechanism configured to maintain a constant length of said at least one yaw cable and to maintain between said first link and said second link.

2. The surgical tool of claim 1 wherein said at least one yaw cable guide channel has guide channel grooves which restrain said at least one yaw cable from moving laterally relative to said at least one yaw cable guide channel.

3. The surgical tool of claim 1 wherein the at least one yaw cable comprises a first and second yaw cable and the at least one end effector link comprises a first and second end effector link;
   wherein said first yaw cable is coupled to said first end effector link and said second yaw cable is coupled to said second end effector link;
   such that the first yaw cable and second yaw cable can actuate the first and second end effector links in the same or opposite direction about said yaw joint pin.

4. The surgical tool of claim 3 wherein said first link has a first side and a second side, said first side has one first yaw cable guide channel and one second yaw cable guide channel, said second side has one first yaw cable guide channel and one second yaw cable guide channel; and
   wherein said first link is configured such that both of said first yaw cable guide channels are inner guide channels and both of said second yaw cable guide channels are outer guide channels such that on each of said first side and said second side each of said second yaw cable guide channels are positioned to the exterior of each of said first yaw cable guide channels.

5. The surgical tool of claim 4 wherein each of said first yaw cable guide channels and each of said second yaw cable guide channels further comprise two arced guides being generally opposed to each other.

6. The surgical tool of claim 5 wherein one of the two generally opposed arced guides is a large radius arc and the other of said generally opposed arc guides is a small radius arc.

7. The surgical tool of claim 3 wherein said first link has a first side and a second side, and each of said first and second sides has a guide protrusion being positioned between the axis of the pitch joint pin and the end of said pitch joint end; and
   wherein each of said first and second sides has two opposed guide channels such that when said second link is actuated about the pitch joint pin such that said second link is not colinear with said first link, one of said first yaw cable and said second yaw cable is guided by said guide protrusion and the other of said first yaw cable and said second yaw cable is guided by one of said opposed guide channels.

8. The surgical tool of claim 7 wherein the guide protrusion on each of said first and second sides is cylindrical in shape.

9. The surgical tool of claim 7 wherein the guide protrusion on each of said first and second sides is positioned such that said guide protrusion is concentric with the axis of the pitch joint pin.

10. The surgical tool of claim 3 wherein the first and second end effector links are configured such that the first and second end effector links form a set of scissors for incising objects.

11. The surgical tool of claim 3 wherein the first and second end effector links are configured such that the first and second end effector links form a grasping tool.

12. The surgical tool of claim 1 wherein the at least one tensioning mechanism comprises:
a first pulley;
a second pulley;
a tensioning pulley being movable relative to said first pulley and said second pulley, and workably connected to a tensioning device;
wherein said at least one yaw cable passes around said first pulley to said tensioning pulley, passes around said tensioning pulley to said second pulley and passes around said second pulley; and
said tensioning device being able to move said tensioning pulley relative to said first pulley and said second pulley such that the length of said at least one yaw cable between said first pulley and said second pulley changes due to changes in the position of said tensioning pulley.

13. The surgical tool of claim 12 wherein said at least one tensioning mechanism further has a sliding feature being connected to said tensioning pulley such that said tensioning pulley is movable relative to said first pulley and said second pulley.

14. The surgical tool of claim 13 wherein said sliding feature further comprises at least one rail feature and a car connectable to said tensioning pulley such that said car is slidable along one axis relative to said at least one rail.

15. The surgical tool of claim 13 wherein said tensioning device is a spring slide mechanism having a spring being connected at one end to said sliding feature and being connected at the other end to a fixed feature such that the length of said at least one yaw cable between said first pulley and said second pulley decreases when the tension in said at least one yaw cable decreases.

16. The surgical tool of claim 13 wherein said tensioning device is a cam slide mechanism having a cam being rotatable about a cam axis such that the position of said cam controls the position of said sliding feature and said tensioning pulley such that the length of said at least one yaw cable between said first pulley and said second pulley increases when said cam pushes said sliding feature away from said cam axis.

17. The surgical tool of claim 16 wherein said cam is coupled to said pitch cable by a coupling mechanism such that the length of said at least one yaw cable between said first pulley and said second pulley changes with respect to the angle between said first link and said second link.

18. The surgical tool of claim 1 wherein said first joint has a range of motion of at least 180°.

19. The surgical tool of claim 1 wherein said second joint has a range of motion of at least 180°.

20. The surgical tool of claim 1 wherein none of said first link, said second link and said at least one end-effector link have a width that is greater than 5 mm.

21. The surgical tool of claim 1 wherein the pitch cable and at least one yaw cable are composed of any one of CNC milled steel, nylon coated stainless steel or polytetrafluoroethylene coated stainless steel.

22. The surgical tool of claim 1 wherein said surgical tool is for use with a surgical robot.

23. The surgical tool of claim 22 wherein said tensioning mechanism is placed proximal to said surgical robot and said first link is mounted on a distal end of a hollow shaft mounted to said tensioning mechanism such that said surgical tool is spaced away from said tensioning mechanism; and
wherein said pitch cable and said at least one yaw cable are threaded through said hollow shaft from the surgical tool to said tensioning mechanism.

24. The surgical tool of claim 23 wherein said surgical robot further comprises a roll actuator considering to rotate said hollow shaft about a roll axis.

* * * * *